United States Patent
Stein et al.

(10) Patent No.: US 8,268,638 B2
(45) Date of Patent: Sep. 18, 2012

(54) METHODS AND APPARATUSES FOR DETECTING ANALYTES IN BIOLOGICAL FLUID OF AN ANIMAL

(75) Inventors: Adam L. Stein, Venice, CA (US); Jacob M. White, Silver Spring, MD (US)

(73) Assignee: Advantageous Systems, LLC, Pasadena, CA (US)

( * ) Notice: Subject to any disclaimer, the term of this patent is extended or adjusted under 35 U.S.C. 154(b) by 921 days.

(21) Appl. No.: 12/175,147

(22) Filed: Jul. 17, 2008

(65) Prior Publication Data

US 2009/0024019 A1 Jan. 22, 2009

Related U.S. Application Data

(60) Provisional application No. 60/929,940, filed on Jul. 18, 2007.

(51) Int. Cl.
*G01N 33/553* (2006.01)
(52) U.S. Cl. ......... 436/526; 436/518; 436/524; 436/525
(58) Field of Classification Search ................. 436/518, 436/524, 525, 526
See application file for complete search history.

(56) References Cited

U.S. PATENT DOCUMENTS

| | | | |
|---|---|---|---|
| 5,565,215 A | 10/1996 | Gref et al. | |
| 5,922,537 A | 7/1999 | Ewart et al. | |
| 6,190,315 B1 | 2/2001 | Kost et al. | |
| 6,391,643 B1 | 5/2002 | Chen et al. | |
| 6,503,722 B1 * | 1/2003 | Valkirs | 435/7.2 |
| 6,649,419 B1 * | 11/2003 | Anderson | 436/526 |
| 6,887,202 B2 | 5/2005 | Currie et al. | |
| 7,004,901 B2 | 2/2006 | Fish | |
| 7,115,688 B1 | 10/2006 | Mirkin et al. | |
| 7,163,511 B2 | 1/2007 | Conn et al. | |
| 7,214,190 B1 | 5/2007 | Wilson | |
| 7,226,414 B2 | 6/2007 | Ballerstadt et al. | |
| 7,236,812 B1 | 6/2007 | Ballerstadt et al. | |
| 2002/0151043 A1 * | 10/2002 | Gordon | 435/287.2 |
| 2003/0124745 A1 | 7/2003 | Chen | |
| 2004/0067502 A1 | 4/2004 | Guenther et al. | |
| 2004/0086885 A1 | 5/2004 | Lee et al. | |
| 2004/0115709 A1 | 6/2004 | Morozov et al. | |
| 2004/0220456 A1 | 11/2004 | Eppstein | |
| 2006/0015058 A1 | 1/2006 | Kellogg et al. | |
| 2006/0025713 A1 * | 2/2006 | Rosengart et al. | 604/5.02 |
| 2006/0205093 A1 | 9/2006 | Prins | |
| 2007/0105176 A1 * | 5/2007 | Ibey et al. | 435/14 |
| 2007/0122829 A1 | 5/2007 | Ballerstadt et al. | |
| 2008/0214987 A1 * | 9/2008 | Xu | 604/21 |

(Continued)

OTHER PUBLICATIONS

Latham, Andrew H. et al., "Controlling Transport and Chemical Functionality of Magnetic Nanoparticles", Accounts of Chemical Research, vol. 41, No. 3, pp. 411-420, Mar. 2008.

(Continued)

*Primary Examiner* — Melanie J Yu
(74) *Attorney, Agent, or Firm* — Myers Wolin, LLC

(57) ABSTRACT

Methods and devices for detecting an analyte are provided. An analyte binding molecule is fixed to a nanoparticle to form a nanoparticle complex. The analyte binding molecule is capable of binding an analyte. The nanoparticle complex is introduced into one of a circulatory system of an animal or biological fluid of the animal. The analyte is allowed to bind to the nanoparticle complex. The analyte bound nanoparticle complex can be extracted and the presence of the analyte can be detected.

19 Claims, 2 Drawing Sheets

U.S. PATENT DOCUMENTS

2011/0038965 A1* 2/2011 McKay et al. .............. 424/742

OTHER PUBLICATIONS

Kumagai, Michiaki et al., "Iron Hydroxide Nanoparticles Coated with Poly(ethylene glycol)-Poly(aspartic acid) Block Copolymer As Novel Magnetic Resonance Contrast Agents for in Vivo Cancer Imaging", Colloids and Surfaces, vol. 56, pp. 174-181, 2007.

Kohler, Nathan et al., "A Bifunctional Poly(ethylene glycol) Silane Immobilized on Metallic Oxide-Based Nanoparticles for Conjugation with Cell Targeting Agents", American Chemical Society, vol. 126, pp. 7206-7211, 2004.

Bae, Ki Hyun et al., "Oil-Encapsulating PEO-PPO-PEO/PEG Shell Cross-Linked Nanocapsules for Target-Specific Delivery of Paclitaxel", American Chemical Society, vol. 8, pp. 650-656, 2007.

Perez, J. Manuel et al., "Viral-Induced Self-Assembly of Magnetic Nanoparticles Allows the Detection of Viral Particles in Biological Media", American Chemical Society, vol. 125, pp. 10192-10193, 2003.

Ito, Akira et al., "Medical Application of Functionalized Magnetic Nanoparticles", Journal of Bioscience and Bioengineering, vol. 100, No. 1, pp. 1-11, 2005.

Liang, Sheng et al., "Surface Modified Superparamagnetic Iron Oxide Nanoparticles: As a New Carrier for Bio-Magnetically Targeted Therapy", J Mater Sci: Mater Med vol. 18. pp. 2297-2302, 2007.

Gupta, Ajay Kumar et al., "Synthesis and Surface Engineering of Iron Oxide Nanoparticles for Biomedical Applications", Biomaterials, vol. 26, pp. 3995-4021, 2005.

Lu, An-Hui et al., "Magnetic Nanoparticles: Synthesis, Protection, Functionalization, and Application", Angew. Chem. Int. Ed. vol. 46, pp. 1222-1244, 2007.

Baroli, Biancamaria et al., "Penetration of Metallic Nanoparticles in Human Full-Thickness Skin", The Society of Investigative Dermatology, pp. 1-12, 2007.

Barnes, Allison L. et al., "Magnetic Characterization of Superparamagnetic Nanoparticles Pulled Through Model Membranes", Biomagnetic Research and Review, vol. 5, Issue 5, Jan. 4, 2007.

Woo, Kyoungja et al., "Easy Synthesis and Magnetic Properties of Iron Oxide Nanoparticles", Chem. Mater. vol. 16, No. 14, American Chemical Society, pp. 2814-2818, 2004.

Iida, Hironori et al., "Synthesis of $Fe_3O_4$ Nanoparticles with Various Sizes and Magnetic Properties by Controlled Hydrolysis", Journal of Colloid and Interface Science, vol. 314, pp. 274-280, 2007.

Hyeon, Taeghwan et al., "Synthesis of Highly Crystalline and Monodisperse Maghemite Nanocrystallites without a Size-Selection Process", J. Am. Chem. Soc. vol. 123, pp. 12798-12801, 2001.

Sun, Shouheng et al., "Monodisperse $MFe_2O_4$ (M = Fe, Co, Mn) Nanoparticles", J. Am. Chem. Soc., vol. 126, pp. 273-279, 2004.

Ma, Hui-li et al., "Preparation and Characterization of Superparamagnetic Iron Oxide Nanoparticles Stabilized by Alginate", International Journal of Pharmaceutics, vol. 333, pp. 177-186, 2007.

Janssen, X.J.A. et al., "On-Chip Manipulation and Detection of Magnetic Particles for Functional Biosensors", Biosensors and Bioelectronics, vol. 23, pp. 833-838, 2008.

Latham, Andrew H. et al., "Capillary Magnetic Field Flow Fractionation and Analysis of Magnetic Nanoparticles", Analytical Chemistry. vol. 77, No. 15, pp. 5055-5062, Aug. 1, 2005.

Reschiglian, Pierluigi et al., "Field-Flow Fractionation and Biotechnology", Trends in Biotechnology, vol. 23, No. 9, Sep. 2005.

Flynn, Edward R. et al., "Use of a SQUID Array to Detect T-Cells With Magnetic Nanoparticles in Determining Transplant Rejection", J Magn Magn Mater, vol. 311, Issue 1, pp. 429-435, Apr. 2007.

Sandhu, Adarsh, "New Probes Offer Much Faster Results", Nature Nanotechnology, vol. 2 pp. 746-748, Dec. 2007.

de Boer, B.M. et al., "An Integrated and Sensitive Detection Platform for Magneto-Resistive Biosensors", Biosensors & Bioelectronics, vol. 22, pp. 2366-2370, 2007.

Burg, Thomas P. et al., "Weighing of Biomolecules, Single Cells and Single Nanopartilces in Fluid", Nature Publishing Group, vol. 446, pp. 1066-1069, Apr. 26, 2007.

* cited by examiner

METHODS AND APPARATUSES FOR DETECTING ANALYTES IN BIOLOGICAL FLUID OF AN ANIMAL

CROSS-REFERENCE TO RELATED APPLICATIONS

This applications claims priority to Provisional Application No. 60/929,940, filed Jul. 18, 2007, which is incorporated herein by reference.

BACKGROUND

Current methods for detecting analytes in blood are invasive and often require a lab setting and can be time consuming. For example, many of the current methods for detecting blood glucose levels require puncturing the skin to extract blood. Also, identification of pathogens which may be used for acts of bioterrorism rely on physical examination and laboratory techniques such as enzyme-linked immunosorbent assay (ELISA) or immunohistochemistry (IHC). While such techniques for identification of such pathogens may be effective, they are invasive and time consuming.

Magnetic nanoparticles are becoming useful in the medical field. Currently, magnetic nanoparticles have such experimental applications as magnetic resonance imaging contrast enhancement, drug delivery, hyperthermia to kill cancer cells selectively, cell separation/cell labeling, magnetofection, and other applications. External magnetic fields have been used to target functionalized magnetic nanoparticles to cancers for diagnosis and treatment with chemotherapeutic agents. Current medical applications for nanoparticles require invasive injection of the nanoparticles into the bloodstream.

It would be desirable to have a device and method for detecting analytes in the circulatory system of an animal that is minimally invasive.

DETAILED DESCRIPTION

Figure 1A:
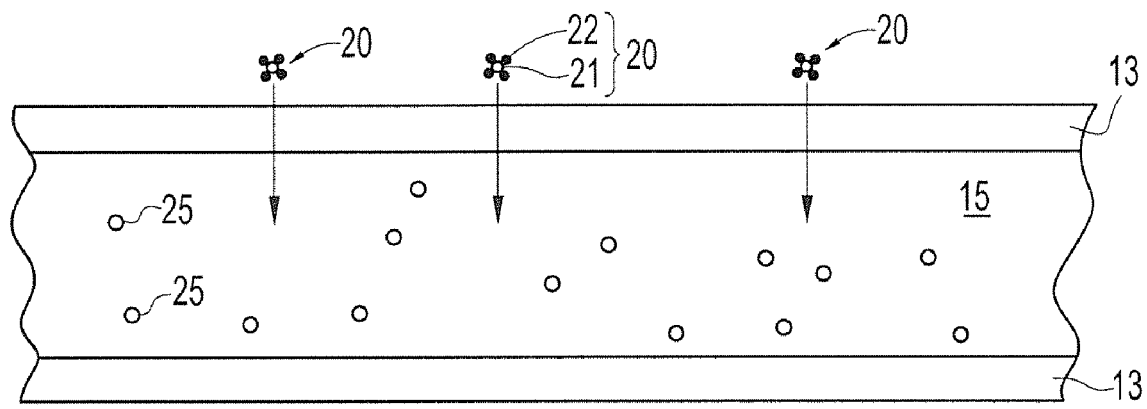
FIGS. 1A and 1B depict methods of inserting nanoparticle complexes and extracting analyte bound nanoparticle complexes and unbound nanoparticle complexes.

The disclosed devices and methods provide for the use of magnetic nanoparticles in detecting analytes found in blood or biological fluid of an animal.

Magnetic nanoparticles can be functionalized by conjugating a binding molecule to the nanoparticle to form a nanoparticle complex. Nanoparticle complexes can be introduced into the blood or other biological fluid, such as interstitial fluid and urine, of an animal. In one case, an external magnetic force is used to introduce the nanoparticle complex into the animal in a minimally-invasive manner. Alternatively, other known methods for inserting the nanoparticle complexes can be used. Once in the blood or biological fluid of the dermis, analytes found in blood or biological fluid bind to the analyte binding molecules of the nanoparticle complexes forming analyte bound nanoparticle complexes. In one case, the analyte bound nanoparticle complexes are extracted from the blood or biological fluid through the dermis using magnetic force. Thus, there is no need for needles or other more invasive insertion or extraction methods.

The analyte bound nanoparticle complexes can be analyzed using various detection techniques. In one case, physical rather than chemical methods of detection are used. For example, nanomechanical resonators, GMR sensors, field flow fractionation followed by SQUID magnetometry can be used to detect an analyte and its concentration. In another case, affinity chromatography column followed by ELISA is used to detect an analyte and its concentration.

Alternatively, analysis of analyte bound nanoparticle complexes can be conducted while the analyte bound nanoparticle complexes remain in the biological fluid or circulatory system of the animal as described in more detail herein.

The disclosed methods and devices are suitable for the diagnosis of pathogens, HIV/AIDS, certain cancers, various autoimmune diseases, and other bacterial or viral diseases currently diagnosed by blood tests, as well as the detection of other molecules found in blood or biological fluid, such as glucose or metabolites.

As used herein "analyte binding molecule" or "binding molecule" includes molecules and compounds that bind or associate with an analyte to be detected. Examples include proteins (e.g., viral surface proteins, cancer cell surface proteins and bacterial proteins), antibodies, targeting ligands, viral antigens, bacterial antigens, nucleic acids (e.g., double stranded DNA, cDNA, RNAi, mRNA), toxin antigens, biomarkers or any other molecule complement.

As used herein "nanoparticle complex" means a magnetic nanoparticle conjugated to or associated with an analyte binding molecule. The nanoparticle complex may or may not include a coating, such as a polyethylene glycol (PEG) coating.

As used herein, the term "introducing" means any method for transporting a nanoparticle complex to the circulation or biological fluid including, but not limited to, injection, infusion, electrochemical repulsion, or pressure.

As used herein, the term "extracting" means any method of removing a nanoparticle complex from the circulation or biological fluid.

Synthesis of Magnetic Nanoparticles

Magnetic nanoparticles according to the description herein, can have various magnetic properties, including but not limited to diamagnetic, paramagnetic, superparamagnetic, ferromagnetic, ferrimagnetic, antiferromagnetic, spin glass, and electromagnetic. The magnetic nanoparticles are made of any suitable magnetic material or combination of materials, such as magnetite, ulvospinel, hematite, ilmenite, maghemite, jacobsite, trevorite, magnesioferrite, pyrrhotite, greigite, troilite, goethite, lepidocrocite, feroxyhyte, iron, nickel, cobalt, awaruite, wairauite, or any combination thereof. The magnetic nanoparticles can be of various size and shape.

Specific magnetic nanoparticles are chosen as desired based on the specific application. The following non-limiting factors are considered in selecting the specific magnetic nanoparticles: ease of synthesis, strong magnetic properties with relatively small diameter, stability and biocompatibility.

In one case, superparamagnetic magnetite ($Fe_3O_4$) nanoparticles are used. The magnetite ($Fe_3O_4$) nanoparticles can be synthesized using a known coprecipitation synthesis method, or other known methods.

In another case, superparamagnetic magnetite ($Fe_3O_4$) and/or maghemite ($\gamma Fe_2O_3$) iron oxide nanoparticles with or without PEG coating are used. Superparamagnetic iron oxide nanoparticles can range in diameter, for example, between about 1 nm and about 500 nm. Such superparamagnetic iron oxide nanoparticles can be produced by high-temperature methods, such as thermal decomposition of a metal precursor in the presence of a stabilizing ligand as a surfactant. Surfactants such as oleic acid and/or oleylamine help prevent agglomeration of the nanoparticles, as well as control growth during synthesis. Metal precursors include, but are not limited to, carbonyl and acetylacetonate complexes ($Fe(CO)_5$ and $Fe(acac)_3$). Thermal decomposition reactions may be conducted in inert atmospheres. Subsequent to thermal decomposition, mild oxidation with trimethylamine oxide (($CH_3)_3NO$) at elevated temperatures can be performed. Other synthesis techniques can be used to modify nanoparticle properties as desired, such as, for example, co-precipitation, microemulsion, and hydrothermal synthesis. In another case, other metals such as $Co^{2+}$ or $Mn^{2+}$ to form $CoFe_2O_4$ or $MnFe_2O_4$ are incorporated into the superparamagnetic iron oxide nanoparticles.

In one case, a mixture of different types and/or sizes of nanoparticles can be used. In another example, the nanoparticles are monodispersed.

Surface modifications, such as encasings or coatings, can optionally be made to enhance biocompatibility, stability, linkage of analyte binding compound, particle-particle interactions, increased blood circulation time, and internalization efficiency. In one case, the magnetic nanoparticles are coated with PEG using known techniques. Other encasings and coatings include polymers, dextran, polyvinylpyrrolidone, fatty acids, polyvinyl alcohol, polyacrylic acid, polypeptides, phosphorylcholine, poly(d,l-lactide), poly(n isopropylacrylamid), chitosan and gelatin.

Formation of Nanoparticle Complexes

To form nanoparticle complexes, the magnetic nanoparticles can be fixed to or associated with analyte binding molecules. In one case, analyte-binding molecules are conjugated to the PEG coating by known methods, such as covalent conjugation via a bifunctional molecular crosslinker or non-covalent conjugation using electrostatic interactions. The specific analyte binding molecule is chosen based on the analyte to be detected.

In one case, a protein or molecule that binds glucose onto its surface (e.g., glucose binding protein or concanavalin A) is attached to PEG coated superparamagnetic magnetite ($Fe_3O_4$) and/or maghemite ($yFe_2O_3$) iron oxide nanoparticles. In another case, the nanoparticle complexes comprise PEG coated magnetic nanoparticles and antibodies targeting virus or bacterial antigens. Antibody and target virus pairs can include: anti-HIV antibody and HIV virus; anti-viral hemorrhagic fevers and viral hemorrhagic fevers (ebola); anti-influenza antibody and influenza virus; anti-smallpox antibody and smallpox virus; anti-HPV antibody and HPV virus, among others. Antibody and target bacteria pairs can include: anti-anthrax antibody and anthrax (bacterium *Bacillus anthracis*); anti-bubonic plague antibody and bubonic plague (bacterium *Yersinia pestis*); anti-tularemia antibody and tularemia (bacterium *Francisella tularensis*); anti-*Escherichia coli* antibody and *Escherichia coli*, among others. In yet another case, the nanoparticle complexes comprise PEG coated magnetic nanoparticles and viral surface proteins that target and bind to antibodies found in blood or biological fluid.

Introduction and Extraction of Nanoparticles

As illustrated in FIG. 1A, a magnetic field is applied to the magnetic nanoparticle complexes 20 (including the magnetic nanoparticle 21 and the binding molecule 22) using magnet 10 to introduce nanoparticle complexes 20 through the skin 13 (inducing the dermis and epidermis) into the circulatory system 15 or biological fluid of an animal. Alternatively, the magnetic nanoparticle complexes 20 can be introduced in any known manner, for example, by injection, electrochemical repulsion or pressure.

Figure 1B:
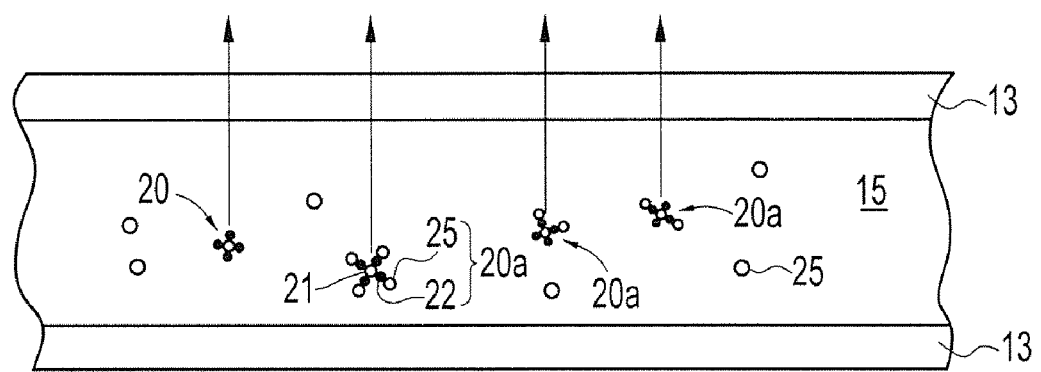

As illustrated in FIG. 1B, after sufficient time to allow for the analyte 25 to bind the binding molecule 22 of the nanoparticle complex 20, the analyte bound nanoparticle complexes 20a and unbound nanoparticle complexes 20 are extracted by the application of a magnetic field using magnet 10. Use of the magnetic field to insert the nanoparticle complexes 20 and extract the analyte bound nanoparticle complexes 20a and unbound nanoparticle complexes 20 is minimally invasive. That is, the skin of the animal need not be pierced as is required in conventional methods of introducing or extracting material from the circulatory system 15 or biological fluid of the animal.

While the magnet 10 is shown pushing the magnetic nanoparticle complexes 20 through the skin 13, it should be understood that alternative placement of the magnet 10 is possible. For example, the magnet 10 can be located on an opposite side of the animal from the magnetic nanoparticle complexes 20 to pull the magnetic nanoparticle complexes 20 through the skin 13. Additionally, although only one magnet 10 is shown, a plurality of magnets can be used in any configuration to supply a plurality of magnetic fields.

Alternatively, the analyte bound nanoparticle complexes 20a need not be extracted and can be detected within the circulatory system 15 or biological fluid of the animal as described in more detail below.

The magnetic field used for introducing and extracting magnetic nanoparticle complexes can be supplied in any known manner. In one case, the magnetic field is between about 100 Gauss and about 20000 Gauss. In another case, rare earth magnets and/or electromagnets are used to provide the magnetic field. Electromagnets, which provide a range between about 500 Gauss and about 1500 Gauss, or rare earth permanent magnets, which provide a range between about 500 Gauss and about 5000 Gauss can be used to insert and extract the magnetic nanoparticle complexes. Alternatively, a superconducting electromagnet can be used.

Figure 2:
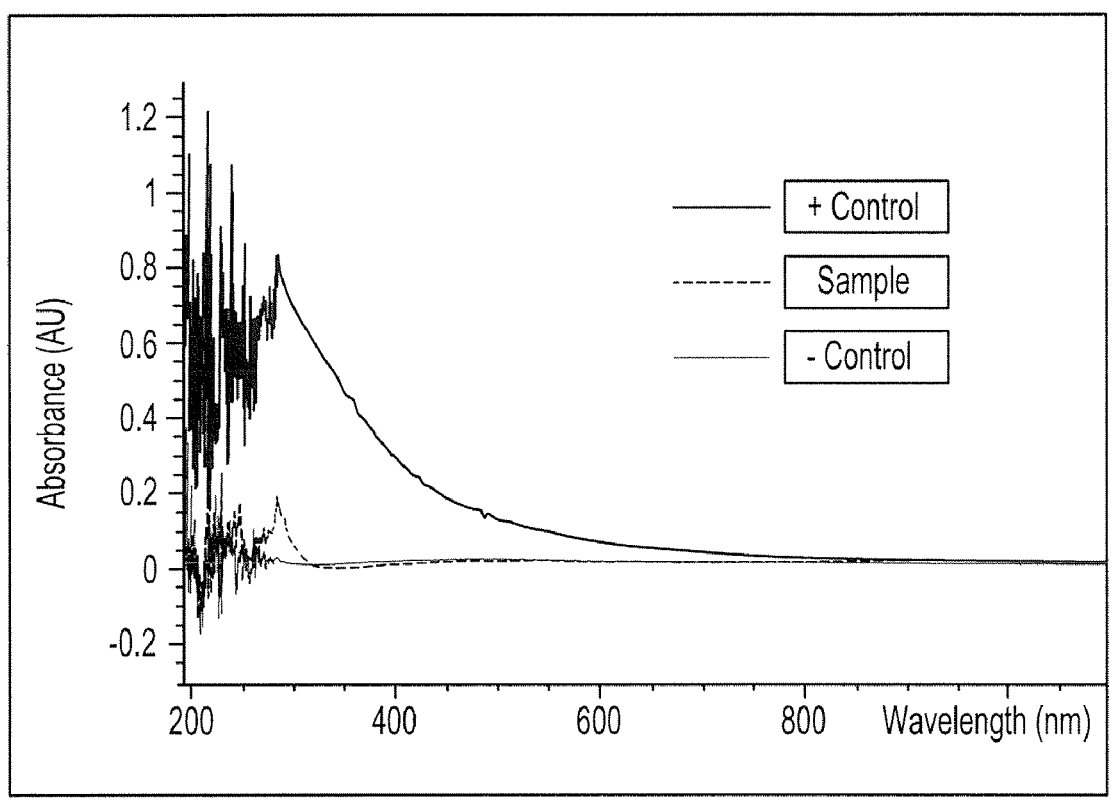
FIG. 2 is a graph illustrating the detection of magnetic nanoparticles passed through the dermis of a mouse by application of a magnetic field.

As shown in FIG. 2, 10 nm $yFe_2O_3$ nanoparticles (usually less magnetic than $Fe_3O_4$) pass completely through both the epidermis and dermis layers of mouse skin under influence of an external magnetic field. Studies were conducted using a vertical diffusion column and four rare earth ring magnets with a collective 800 Gauss magnetic field. Detection of nanoparticles monodispersed in a toluene collection vial was accomplished by UV spectroscopy. FIG. 2 is a graph of the UV spectroscopic results. The positive control included 70 μL of magnetic nanoparticles monodispersed in toluene, the negative control was toluene without nanoparticles.

Nanoparticle complexes can be introduced into the circulatory system or biological fluid of an animal in a minimally-invasive manner using electrochemical repulsion whereby an external charge (e.g., of the same type as the nanoparticle complexes) provides the force needed to introduce the nanoparticle through the dermis. Alternatively; pressure (e.g., using a needle-free air syringe or similar device) can be used to introduce the nanoparticle complexes. Nanoparticle complexes can also be introduced by injection or infusion.

Analysis of Analyte Bound Nanoparticle Complexes

Physical and chemical characteristics of the analyte bound nanoparticle complexes can be used to detect the analyte and, optionally, measure its concentration. Physical detection mechanisms include nanomechanical resonators, giant magnetoresistance (GMR) sensors, and field flow fractionation followed by SQUID (superconducting quantum interference device) magnetometry. Chemical detection techniques include using affinity chromatographic procedures to elute the analyte, followed by analysis of the eluted analyte by, e.g., ELISA or other techniques.

In one case, a nanomechanical resonator is used. Nanomechanical resonators measure mass with great sensitivity by detecting oscillations of a cantilever. Nanoparticle complexes are weighed as they pass through the cantilever of the nanomechanical resonator. The weight of the analyte bound nanoparticle complexes will be greater than that of the unbound nanoparticle complexes. Accordingly, the detected weights will indicate the presence and amount of the analyte.

Microchannels are created by making buried channels in silicon-on-insulator wafers followed by wafer thinning and dry etching. Many microchannels will be produced on a wafer and electrostatic drive electrodes placed under each cantilever. Detection of cantilever vibration will be done optically while cantilevers are driven electrostatically at different frequencies. Vibration amplitude will be monitored with a laser and position sensitive photodetector.

In another case, a GMR sensor is used to detect analytes bound to nanoparticle complexes. GMR sensors are used in electronic device hard-disk drives and use the properties of magnetic resistance of magnetic bits arranged in sectors on concentric tracks of the disk that can be read with a GMR reading head. In one example, a GMR sensor will be configured as a biosensor having analyte binding molecules that are fixed to the GMR sensor surface for targeting analyte bound nanoparticle complexes by attaching to the exposed section of the analyte, thereby forming a sandwich of the GMR fixed analyte binding molecule/analyte/nanoparticle complex. Fixed analyte binding molecules that do not bind to an extracted analyte bound nanoparticle complex can be washed off the sensor surface. The remaining fixed analyte binding molecules bound to an extracted analyte bound nanoparticle complex can then be detected using a GMR reading head.

The GMR biosensor can include a GMR magnetic field sensor with two current wires on either side manufactured on a silicon substrate. A layer of silicon nitride is provided to insulate the sensors and wires protecting them from the nanoparticle complex fluid solution. A thin layer of gold is fabricated above the silicon nitride layer acting as a surface for cross-linkage to fixed analyte binding molecules that will attach to analyte bound nanoparticle complexes of the solution. Analyte bound nanoparticle complexes in solution can be placed in proximity with the analyte binding molecules on the biosensor surface for a sufficient amount of time to allow for binding of the analytes of the nanoparticle complexes to the analyte binding molecules fixed on the sensor surface. After nanoparticle complexes that do not bind are washed off, an electrical force can be applied to the wires thereby magnetizing the nanoparticle complexes bound to the sensor surface. When the magnetic nanoparticles are magnetized, their dipole-field causes a change in resistance that is read by the GMR reading head.

In one case, antibodies targeting viral antigens can be used as fixed binding molecules fixed onto the GMR biosensor for nanoparticle complexes targeting viral antigen analytes in blood or biological fluid. In another case, anti-human secondary antibodies are used as fixed binding molecules for nanoparticle complexes targeting antibodies found in blood or biological fluid. The amount of magnetic nanoparticles read on the GMR sensor can determine the presence and amount of the analyte.

In another case, field flow fractionation followed by SQUID magnetometry is used. Field flow fractionation is a technique used to separate various sized molecules and cells using the properties of the different flow rates in a fractionation tube with a cross flow stream pushing the molecules to different areas on an accumulation wall. Thus, heavy analyte bound nanoparticle complexes will flow through a fractionation tube in an axial carrier liquid slower than unbound nanoparticle complexes and bound and unbound nanoparticle complexes can be divided into different accumulation vials under the accumulation wall. The accumulated solutions with bound or unbound nanoparticle complexes can be analyzed using a SQUID to detect the magnetic moments of the nanoparticle complexes. Alternatively, asymmetrical field flow fractionation can be used.

A brief magnetizing field can be applied to the nanoparticle complexes in respective accumulation vials and decaying remnants of magnetic fields emanating from individual nanoparticle complexes are detected by the SQUID. SQUIDs are sensitive enough to detect individual magnetic nanoparticle moments and therefore can be used to analyze and count analyte bound nanoparticle complexes after separation by field flow fractionation.

In another method, analyte can be removed from the nanoparticle complex and eluted for further analysis using chromatography procedures. For example, the nanoparticle complex bound to analyte can be passed through a column where the nanoparticle complex binds to a stationary phase within the column and the analyte passes through the column. Alternatively, the exposed section of analyte can bind to the stationary phase and the nanoparticle complexes eluted and then the analyte can be eluted in a subsequent step. The analyte can then be detected and its concentration measured using any appropriate technique. In one case, the analyte detected is glucose and, once the glucose is eluted, glucose oxidase is used to break down glucose yielding hydrogen peroxide and gluconic acid. The hydrogen peroxide then reacts with a dye-based oxygen acceptor thereby causing a color change proportionate to the concentration of glucose. The concentration of glucose can then be determined using spectrometric techniques. In another case, the glucose oxidation reaction, and thereby the glucose concentration, is detected using an electrochemical cell that measures the current produced by the glucose oxidation reaction. In another case, the analyte is a nucleic acid detected using PCR.

In another case, chromatography is followed by ELISA to detect, for example, an antibody or antigen.

Alternatively, nanoparticle complexes with antibodies as analytes can be immediately tested in an ELISA without prior chromatographic techniques to isolate the analyte. This is due to the fact that anti-human secondary antibodies coupled with fluorescence can immediately bind to the exposed Fe region of the viral antibody using ELISA techniques and be immediately assessed for magnitude of fluorescence without the need to separate the analyte from the nanoparticle complex.

In another case, analyte bound nanoparticle complexes can be detected in the circulatory system of an animal or biological fluid of the animal without removing the nanoparticle complexes from the biological fluid. That is, the analyte bound nanoparticle complexes can be detected prior to removal or are not removed. An external device is used to detect analyte bound nanoparticle complexes using, for example, Raman Spectroscopy, external magnets and SQUID magnetometry. In instances where the analyte bound nanoparticle complexes absorb a different wavelength of light or electromagnetic radiation than unbound nanoparticle complexes, the analyte bound nanoparticle complexes can be detected by spectrophotometric means by passing light or electromagnetic radiation through a portion of the animal and measuring the absorption of the light or electromagnetic radiation.

External detection of the analyte bound nanoparticle complexes is particularly desirable when analyte bound nanoparticle complexes are too large to extract or there is toxicity associated with transdermal nanoparticle complex extraction. Additionally, external detection can be faster, less expensive and more convenient than extracting the analyte bound nanoparticle complexes.

Diagnostic Device

Figure 3:
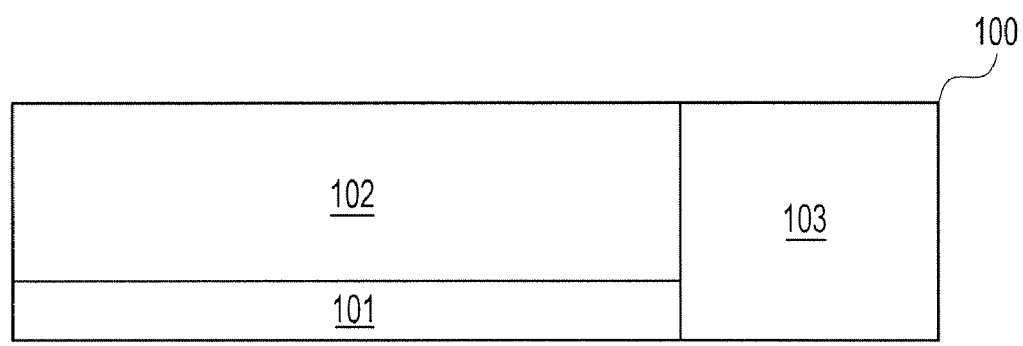
FIG. 3 is a block diagram of a device for detecting analytes in the circulatory system of an animal.

A device 100 for carrying out the insertion and extraction of the nanoparticle complexes is shown in FIG. 3. The device 100 includes a container 101 of nanoparticle complexes specific to an analyte to be detected. Illustratively, the nanoparticle complexes are monodispersed. The device 100 also includes a magnet 102 for supplying the magnetic field for introducing and extracting the nanoparticle complexes. A detection apparatus 103 is also included for analyzing the extracted nanoparticle complexes and determining the presence and, optionally, the amount of the analyte bound to the extracted nanoparticle complexes. Illustratively, the device 100 is portable.

While the device 100 is depicted as a single structure, it should be understood that the components can be modular such that the detection apparatus 103 can be separated from the container 101 and/or magnet 102.

In one example, the detection apparatus 103 utilizes physical properties rather than chemical properties to distinguish bound and unbound nanoparticle complexes. In the illustrated example, the detection apparatus 103 is a giant magnetoresistance (GMR) sensor.

What is claimed as new and desired to be protected by Letters Patent of the United States is:

1. A method of detecting an analyte comprising the steps of:
    providing at least one nanoparticle, wherein the nanoparticle is magnetic;
    fixing at least one analyte binding molecule to the at least one nanoparticle to form a nanoparticle complex, the at least one analyte binding molecule being capable of binding an analyte;
    introducing the nanoparticle complex into a circulatory system of an animal or biological fluid within the animal;
    allowing the analyte to bind to the at least one analyte binding molecule within the animal to form an analyte bound nanoparticle complex;
    extracting the analyte bound nanoparticle complex prior to detecting the analyte wherein at least one of the acts of introducing and extracting the nanoparticle complex comprises using a magnetic field to move the nanoparticle complex through the skin of the animal; and
    detecting the presence of the analyte.

2. The method of claim 1, wherein the at least one nanoparticle is selected from the group consisting of: superparamagnetic magnetite ($Fe_3O_4$), and maghemite ($yFe_2O_3$) iron oxide nanoparticles.

3. The method of claim 2, wherein the at least one nanoparticle further comprises one of $Co^{2+}$ and $Mn^{2+}$.

4. The method of claim 1, wherein the at least one nanoparticle has a polyethylene glycol coating.

5. The method of claim 1, wherein the at least one nanoparticle is coated with a material selected from the group consisting of: polymers, dextran,-polyvinylpyrrolidone, fatty acids, polyvinyl alcohol, polyacrylic acid, polypeptides, phosphorylcholine, poly(d,l-lactide), poly(n-isopropylacrylamid), chitosan and gelatin.

6. The method of claim 1, wherein the analyte is a glucose, and the at least one analyte binding molecule is one of concanavalin A and a glucose binding protein.

7. The method of claim 1, wherein the at least one analyte binding molecule is an antibody and the analyte is one of a virus antigen and bacterial antigen.

8. The method of claim 1, wherein the at least one analyte binding molecule is one of a viral surface protein, cancer cell surface protein and bacterial protein and the analyte is an antibody.

9. The method of claim 1, wherein introducing the at least one nanoparticle does not require piercing the skin of the animal.

10. The method of claim 1, further comprising determining a concentration of the analyte.

11. The method of claim 1, wherein the magnet field is between about 100 Gauss and about 20000 Gauss.

12. The method of claim 1, further comprising providing the magnetic field using one of a rare earth magnet or an electromagnet.

13. The method of claim 1 wherein the presence of the analyte is detected by one of a nanomechanical resonator, a giant magnetoresistance sensor, and a field flow fractionation technique followed by SQUID magnetometry.

14. The method of claim 1, wherein the presence of the analyte is detected by ELISA techniques.

15. The method of claim 14, wherein the detection of the analyte further comprises using chromatographic techniques to elute the analyte prior to using the ELISA techniques.

16. The method of claim 1, further comprising removing the biologic fluid from an animal and at least one of the acts of introducing and extracting the nanoparticle complex using a magnetic field to move the nanoparticle complex through the biologic fluid.

17. The method of claim 1, wherein the presence of the analyte is detected by PCR techniques.

18. The method of claim 1, wherein the at least one nanoparticle is between about 1 nm and about 500 nm in diameter.

19. The method of claim 18, wherein the at least one nanoparticle is between about 1 nm and about 10 nm in diameter.

* * * * *